United States Patent [19]

Hasegawa

[11] Patent Number: 4,851,689

[45] Date of Patent: Jul. 25, 1989

[54] PHOTODETECTING CIRCUIT

[75] Inventor: Kazuo Hasegawa, Furukawa, Japan

[73] Assignee: Alps Electric Co., Ltd., Japan

[21] Appl. No.: 137,414

[22] Filed: Dec. 23, 1987

[30] Foreign Application Priority Data

Apr. 15, 1987 [JP] Japan .................................. 62-92740

[51] Int. Cl.$^4$ ......................... H01J 40/14; G01V 9/04
[52] U.S. Cl. ................................. 250/214 B; 250/221
[58] Field of Search ............... 250/214 B, 214 A, 221, 250/222.1; 307/311; 340/555–557

[56] References Cited

U.S. PATENT DOCUMENTS

| | | | |
|---|---|---|---|
| 4,061,925 | 12/1977 | van der Gaag et al. | 250/214 B |
| 4,417,148 | 11/1983 | Otake | 250/214 B |
| 4,713,534 | 12/1987 | Masters et al. | 250/214 B |

*Primary Examiner*—David C. Nelms
*Assistant Examiner*—Michael Messinger
*Attorney, Agent, or Firm*—Guy W. Shoup; Paul J. Winters; Stephen L. Malaska

[57] ABSTRACT

A photodetecting circuit for detecting radiation emitted from a light emitting element in the presence of ambient radiation is disclosed. The circuit includes a first and a second synchronizing on/off input signal having a predetermined period, each signal being complementary to the other. When the first synchronizing signal is "on", the second synchronizing signal is "off" and the circuit can detect the amount of ambient radiation. When the first synchronizing signal is "off", the second synchronizing signal is turned "on" and the light emitting element is energized and the circuit detects the amount of radiation emitted therefrom. The circuit prevents erroneous readings of radiation emitted from the light emitting element when the amount of detected ambient radiation is high.

8 Claims, 4 Drawing Sheets

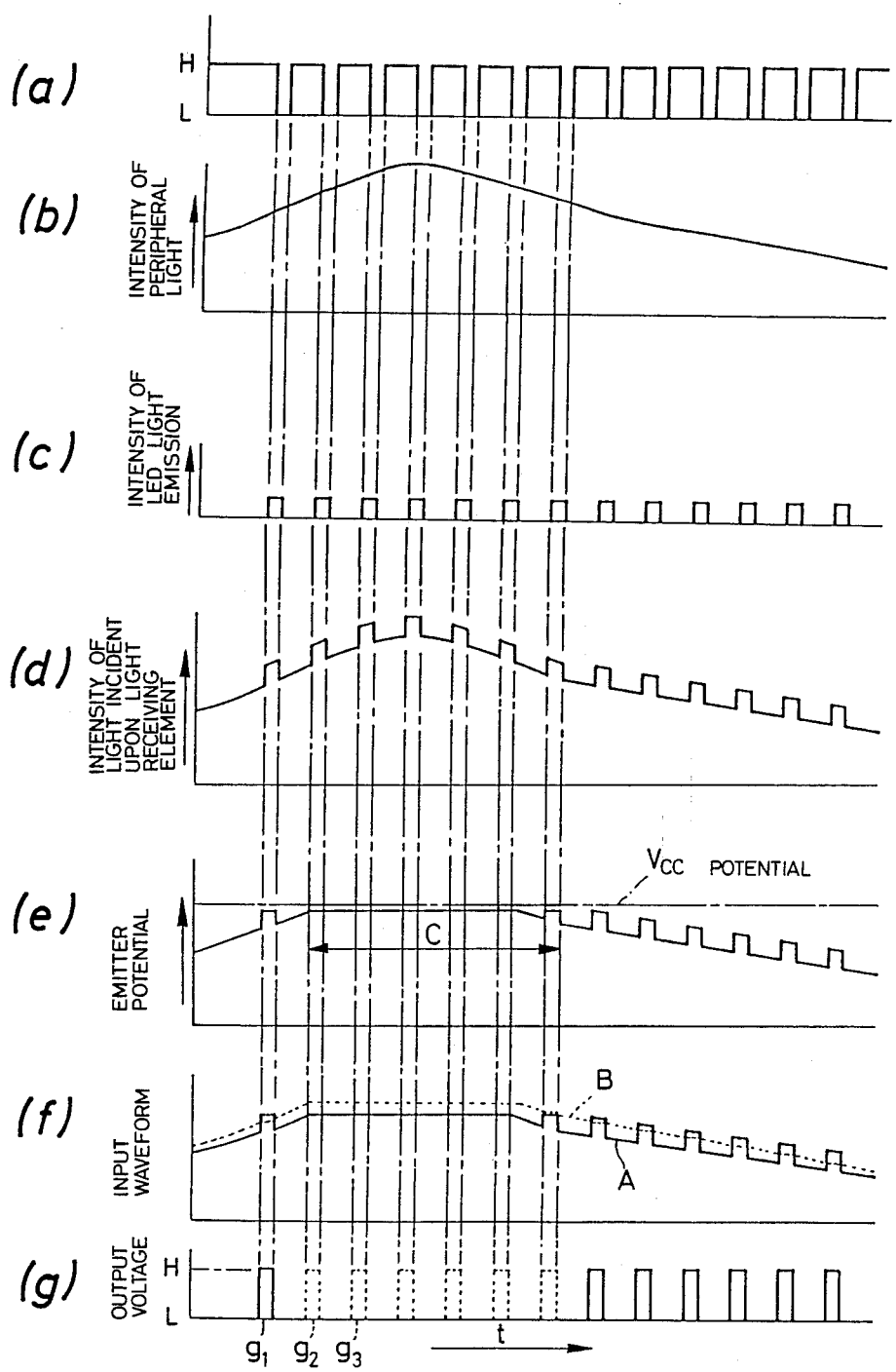

PHOTODETECTING CIRCUIT

BACKGROUND OF THE INVENTION

1. Field of the Invention

The present invention generally relates to a photodetecting circuit such as a photoconductive switch and an optical type position detecting apparatus where light illuminated from a light emitting element is photoelectrically detected via detecting space by a light receiving element, and, more particularly, to a photodetecting circuit capable of preventing erroneous operations of the photodetecting circuit under higher intensity of peripheral light.

2. Description of the Related Art

In a photoconductive switch and an optical type position detecting apparatus, a light emitting element is positioned either, directly opposite to a light receiving element, or indirectly opposite to the light receiving element by employing a reflecting mirror and an optical fiber so as to form an optical beam in detecting space. Then, an output signal such as an interruption signal and a position signal is obtained, which represents such a fact that an optical beam originated from the light emitting element is not transferred to the light receiving element, by detecting the interruption of the optical beam.

Normally, a visual, or an infrared light emitting diode is employed as the light emitting element, and a phototransistor, or a photodiode is utilized as the light receiving element in the photoconductive apparatus.

Since the photodetecting circuit of the photoconductive apparatus includes opening space for detecting the incident light, it may be adversely influenced by not only the light transferred from the light source, but also unwanted light, e.g., the illumination around the opening space (i.e., peripheral light). Various types of the conventional methods for eliminating the peripheral light have be so far proposed. In, for instance, Japanese examined (KOKOKU) patent application No. 61-25161, there is disclosed the threshold level controlling type photodetecting circuit.

The above-described published conventional photodetecting circuit will now be summarized with reference to drawings.

FIG. 3 is a circuit diagram of the prior art photodetecting circuit, and FIG. 4 illustrates waveforms to explain various operations of the circuit shown in FIG. 3.

To describe the circuit arrangement shown in FIG. 3, reference numeral 1 denotes an inverting logic circuit; reference numeral 2 indicates an analog comparator circuit (referred to as "a comparator circuit"); a symbol "CL" represents a synchronizing signal line; a symbol "C2" is a capacitor; a symbol "LED" indicates a light emitting diode; a symbol "PTR" represents a light receiving element; a symbol "Q" is a transistor; symbols "R3" to "R8" are resistors; a symbol "S" represents a switching circuit; and a symbol "Vcc" indicates a power supply line.

In the circuit shown in FIG. 3, one terminal of a series circuit constructed by the light emitting diode LED and the resistor R3 is connected to a positive power supply line, whereas the other terminal thereof is connected to a collector of an NPN bipolar transistor Q. To a base electrode of this transistor Q, one end of the resistor R4 is connected; the other end of which resistor R4 is connected to the output terminal of the inverting logic circuit 1 (will be discussed later). The base electrode of the transistor Q is grounded via the resistor R5. An emitter of this transistor Q is also grounded. The above-described circuit arrangement will drive the light emitting diode LED when the output of the inverting logic circuit 1 becomes a high level.

Then, the circuit arrangement of the light receiving circuit will now be described. The light receiving element PTR is an NPN type bipolar phototransistor. A collector of this bipolar phototransistor is connected to the positive power supply line Vcc, whereas a base electrode of the phototransistor functioning as the light detecting section, is so arranged as to receive the light emitted from the light emitting diode (element) LED. An emitter of this light receiving element PTR is grounded via the resistor R6. A junction between this emitter and the resistor R6 is connected to each one end of the resistor R7 and the switching circuit S. The other end of the resistor R7 is connected to a non-inverting input (+) of the comparator circuit 2. This non-inverting input (+) of the comparator circuit 2 is grounded via the resistor R8. A signal having a value corresponding to the light receiving amount of the light emitting element PTR is divided by the resistors 7 and 8 and then supplied to the non-inverting input terminal (+).

The other end of the switching element S and one terminal of the capacitor C2 are, one the other hand, connected to the inverting input (−) of this comparator circuit 2. As this switching element S, an analog switch arranged by a field effect transistor (FET) is employed. The switching element S has first and second terminals which are conductive in both ways, and a third terminal. When a high level voltage is applied to the third terminal of the switching element S, a minimum impedance is present between the first and second terminals thereof. The first terminal of the switching element "S" is connected to the emitter of the above-described light emitting element PTR, and the second terminal thereof is connected to the inverting input (−) of the above-mentioned comparator circuit 2, and furthermore, the third terminal thereof is connected to the synchronization signal line CL in combination with the input of the above-identified inverting logic circuit 1. Since the inverting input (−) of the comparator circuit 2 is grounded via the above-described capacitor C2, the voltage produced while the switching element "S" is closed, is held by the capacitor C2 which is so arranged as a sample-and-hold circuit fuctioning when the switching element "S" is opened.

The comparator circuit 2 compares the noninverting input (+) with the inverting input (−) supplied via the sample-and-hold circuit, and then outputs a high level signal when the voltage of the non-inverting input (+) exceeds the inverting input (−), and outputs a low level signal when the voltage of the inverting input (−) is lower than the inverting input.

Operations of the conventional photodetecting circuit shown in FIG. 3 will now be described with reference to the various waveforms illustrated in FIG. 4.

As illustrated in FIG. 4a, a positive rectangular pulse having a predetermined period and a predetermined crest value is input as an input signal to the synchronizing signal line CL. Based upon this clock pulse (a), both the switching circuit "S" and the inverting amplifier 1 supply, as indicated by a dotted line of FIG. 4f, the output signal detected by the light receiving element PTR to the inverting input (−) of the comparator circuit 2, and also turn on and off the light emitting diode LED in a form of a rectangular pulse, as illustrated by a dotted shape of FIG. 4c. It is assumed that the light such as sunlight and lamp light having the intensity (b) of the peripheral light, as shown in FIG. 4(b), is incident upon the light receiving element PTR under the condition of the detecting space where the optical signal emitted from the light emitting diode LED can reach the light receiving element PTR. Under the above-identified condition, the detection signal (e) of the light receiving element PTR acquired by detecting the light having the intensity of the waveform, as shown in FIG. 4d, is divided by the resistors R7 and R8, and the resultant voltage is applied to the non-inverting input (+) of the comparator circuit 2, as illustrated by a solid line of "A" in FIG. 4f.

The voltage is input via the sample-and-hold circuit to the inverting input (−) of the comparator circuit 2 under the following condition. That is to say, this voltage is applied to this comparator circuit 2 while the signal output condition obtained by receiving the peripheral light very close to the light receiving element PTR during the turn-off of the light emitting diode LED, is held only when the light emitting diode LED is turned on.

As a consequence, when the voltage signal "A" being applied to the non-inverting input (+) exceeds the voltage signal "B" being applied to the inverting input (−) of the comparator circuit 2, the high-leveled signal g1 is output as illustrated in FIG. 4g, which represents the non-detection condition. However, even if the peripheral interference light is incident upon the light receiving element PTR, no high-leveled output signal indicating the non-detection condition is produced. This is because only the voltage component divided by the above-described resistors R7 and R8 is applied to the inverting input (−) of the comparator circuit 2, which is lower than the voltage being applied to the non-inverting input (+) thereof under the condition that the optical signal originated from the light emitting diode LED cannot reach the light receiving element PTR.

The above-described conventional photodetecting circuit has however the following great drawbacks.

That is to say, when the peripheral interfering light is incident upon the light receiving element PTR, as illustrated by a range "C" in FIG. 4e, the emitter current of the light receiving element, i.e., phototransistor PTR is saturated at an approximate value defined by the power supply voltage Vcc and the resistor R6, so that the voltage (referred to the symbol "A" in FIG. 4f) being applied to the non-inverting input (+) does not exceed the voltage (referred to the symbol "B" in FIG. 4f) of the inverting input (−) of the comparator circuit 2 although the light come from the light emitting diode LED has reached the light receiving element PTR. Accordingly, since the low-leveled output signals g2 and g3 (see FIG. 4g) representative of the detection condition are output, the erroneous operation will occur inevitably.

It is, therefore, a primary goal of the present invention to provide a photodetecting circuit which can avoid such an erroneous operation that the signal representative of the non-detecting condition is mistakenly output in the conventional circuit when the peripheral interfering light having the higher intensity is received under the detecting condition, and also prevent another erroneous operation that the signal indicating the non-detecting condition is erroneously output in the prior art circuit when the peripheral interfering light having the higher intensity is received under the non-detecting condition.

SUMMARY OF THE INVENTION

The above object and other features of the present invention are accomplished by providing a photodetecting circuit wherein a light emitting element driven in synchronism with a synchronizing signal, a light receiving element for detecting light emitted from the light emitting element, and an output signal is derived for indicating whether or not the light coming from said light emitting element has reached the light receiving element, characterized by comprising:

a current-to-voltage converting circuit for converting a current signal detected by said light receiving element into a corresponding voltage signal;

a first feedback circuit for negative-feeding the output signal of said current-to-voltage converting circuit back to an input circuit of said current-to-voltage converting circuit; and a second feedback circuit for feeding the output signal of said current-to-voltage converting circuit back to the input circuit of said current-to-voltage converting circuit via a sample-and-hold circuit for detecting and holding the output signal of said current-to-voltage converting circuit, based upon said synchronizing signal while the light emitting element does not emit the light.

According to the present invention, under the conditions that the light receiving element PTR receives both the light originated from the light emitting diode LED and the peripheral interfering light having the higher intensity than that of the first-mentioned light, the second negative feedback circuit 4 could cancel the peripheral light component based upon the most approximate current value of the peripheral light obtained when the light emitting diode LED is turned off in case that the light emitting diode LED is turned on. Also, since a predetermined constant value is fed back by the first negative feed back circuit R1, the photocurrent of the light emitting diode LED is converted into the corresponding voltage signal based upon a predetermined current-to-voltage converting coefficient. As a result, the light emitting signal of the light emitting element LED can be stably detected and output.

BRIEF DESCRIPTION OF THE DRAWINGS

For a better understanding of the present invention, reference is made of the following specification in conjunction with the accompanying drawings, in which;

FIGS. 4a, 4b, 4c, 4d, 4e, 4f, and 4g illustrate waveforms of the circuit elements of the photodetecting circuit shown in FIG. 3.

DETAILED DESCRIPTION OF THE PREFERRED EMBODIMENTS

A description will now be made of a photodetecting circuit according to one preferred embodiment of the invention with reference to FIGS. 1 and 2.

Figure 3:
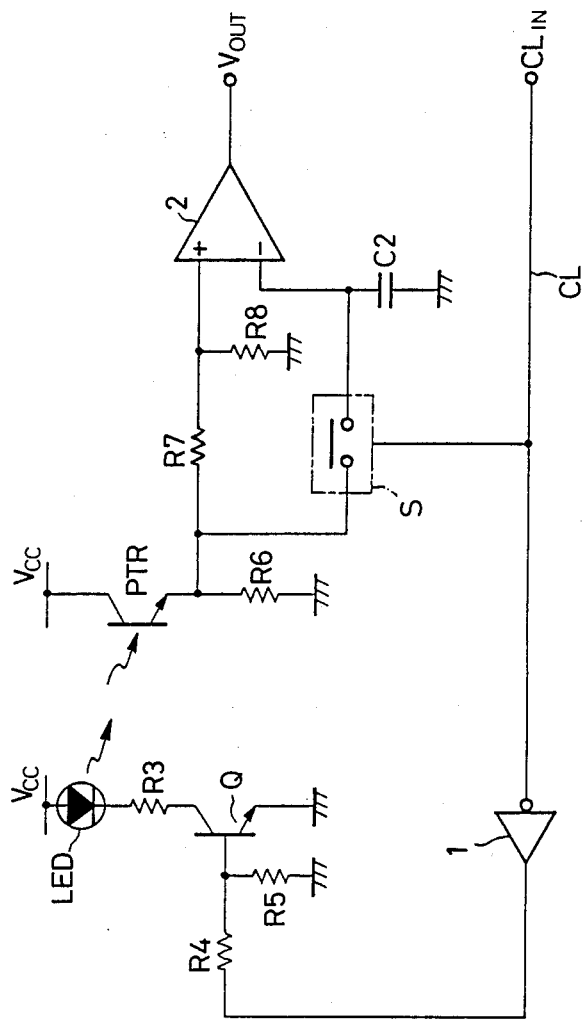
FIG. 3 is a circuit diagram of a conventional photodetecting circuit.

It should be noted that the same reference numerals of FIG. 3 will be employed to denote the same, or similar circuit elements shown in FIG. 1, and no further explanation thereof will be made in the following specification.

Figure 1:
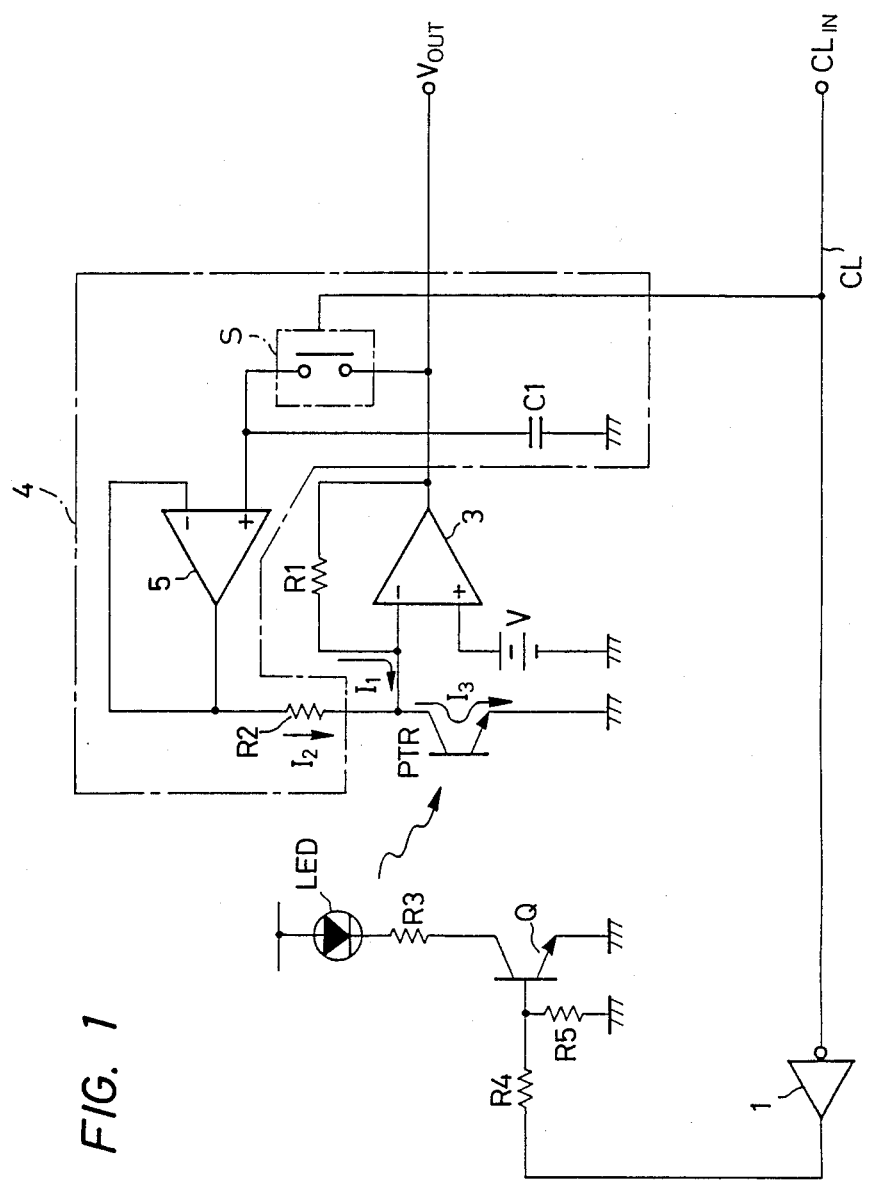
FIG. 1 is a circuit diagram of a photodetecting circuit according to one preferred embodiment of the invention.
Figure 2:
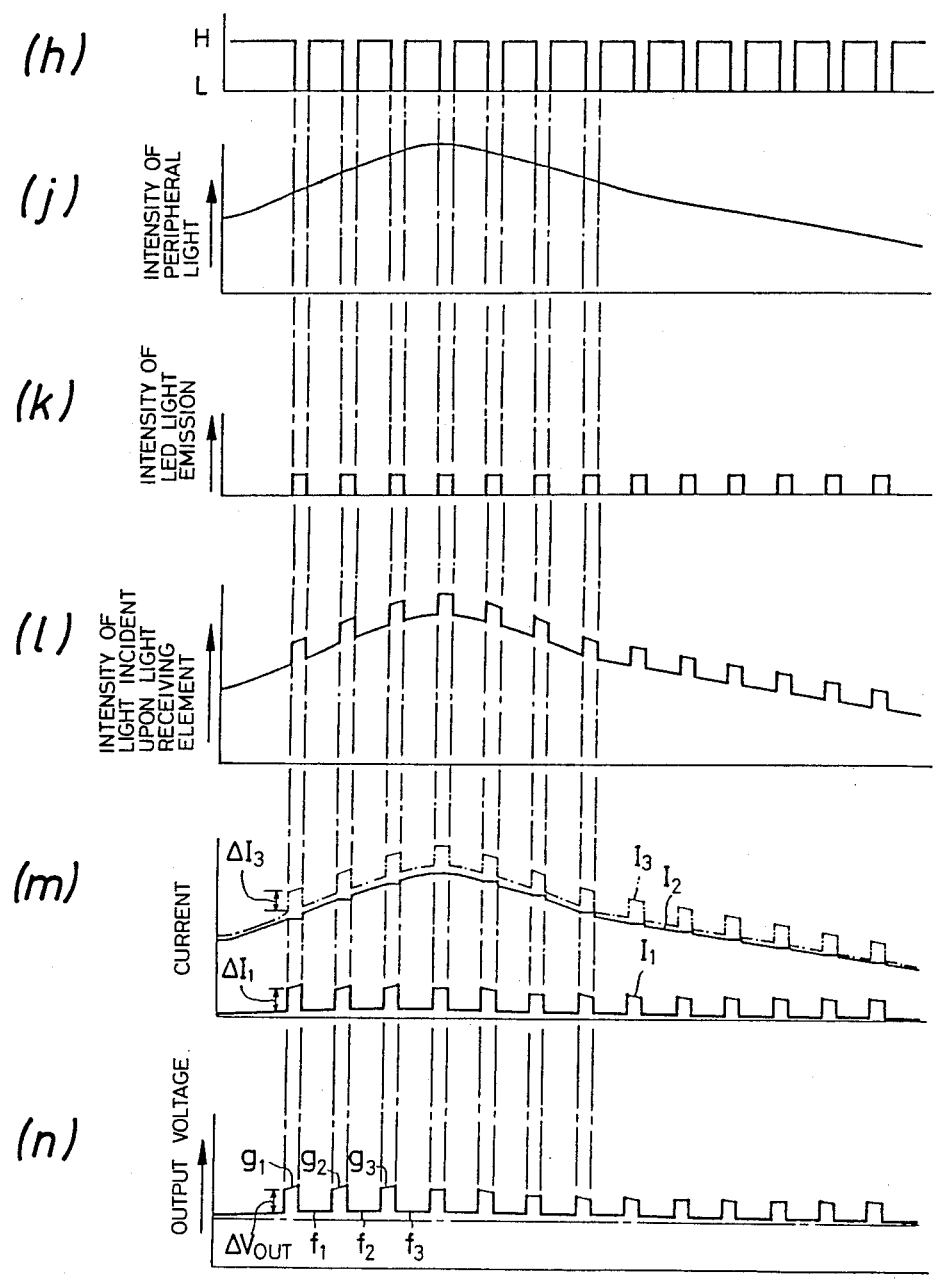
FIGS. 2h, 2j, 2k, 2l, 2m and 2n illustrate waveforms of the circuit elements of the photodetecting circuit shown in FIG. 1.

FIG. 1 is a circuit diagram of the photodetecting circuit according to one preferred embodiment of the invention, and FIG. 2 illustrates waveforms for explaining various operations of the photodetecting circuit shown in FIG. 1. In the circuit of FIG. 1, reference numerals 3 and 5 indicate operational amplifiers, reference numeral 4 indicates a second negative feedback circuit, a symbol "C1" represents a capacitor, a symbol "CL" indicates a synchronizing signal line, a symbol "R1" is a resistor (for a first negative feedback circuit), a symbol "R2" represents a resistor (for the second feedback circuit), a symbol "S" indicates a switching circuit, a symbol "LED" is a light emitting element (diode), a symbol "PTR" denotes a light receiving element, and a symbol "V" indicates a reference voltage circuit.

As easily seen from the circuit diagram shown in FIG. 1, the light emitting diode LED and its driving circuit have the same function as that of the conventional circuit arrangement. That is to say, both the light receiving element PTR and the base arrangement are similar to those of the conventional photodetecting circuit. The emitter of this light receiving element PTR is grounded, whereas the collector thereof is connected to the inverting input (−) of the operational amplifier 3. The non-inverting input (+) of the operational amplifier 3 is connected to a positive polarity of a reference voltage circuit V. This reference voltage circuit V is arranged by, for instance, a constant voltage generating circuit where the power supply voltage is applied via a resistor to, e.g., a zener diode (not shown in detail). A negative polarity of the reference voltage circuit is grounded. To the output of the operational amplifier 3, each end of the first and second negative feedback circuits R1 and 4 is connected. The other end of this resistor R1 is connected to the inverting input (−) of the operational amplifier 3 in order to continuously flow a first feedback current with a constant coefficient through a junction between the light emitting element PTR and the inverting input (−) of the operational amplifier 3. The first feedback current I1 depends upon the output voltage of the operational amplifier 3. A first terminal of a switching circuit "S" of the second feedback circuit 4 is connected to the output of the operational amplifier 3, a second terminal thereof is connected to the non-inverting input (+) of the operational amplifier 5, and a third terminal thereof for a switching control is connected to the synchronizing signal line "CL", respectively. The circuit formed between the first and second terminals of the switching circuit "S" is closed at a switching timing which is completely opposite to the light emitting timing of the light emitting diode LED.

To an non-inverting input (+) of the operational amplifier 5, a positive polarity of a capacitor C1 is connected, and a negative polarity thereof is grounded. Both this operational amplifier 5 and the switching circuit S in conjunction with the capacitor C1 constitute a sample-and-hold circuit. The inverting input (−) of this operational amplifier 5 is short-circuited to the output thereof, so that this operational amplifier 5 functions as a buffer amplifier having an amplification of unity. The output of this operational amplifier 5 is so designed that a second negative feedback current I2 is supplied via a resistor R2 to a junction between the collector of the light receiving element PTR, the resistor R1, and the inverting input (−) of the operational amplifier 3.

The first operational amplifier 3 is arranged to constitute a current-to-voltage converting circuit in such a manner that the first and second negative feedback circuits R1 and 4 having a parallel impedance of "Z" are connected between the output of this operational amplifier 3 and the inverting input (−) thereof. As a result, the current I3 flowing through the light receiving element PTR is substantially equal to a sum (I1+I2) of the first and second negative feedback currents I1 and I2.

Then, a voltage appears at the voltage output Vout of the operational amplifier 3 functioning as the current-to-voltage converting circuit. This voltage is obtained by adding the reference voltage V to a product of the current I3 flowing through the light receiving element PTR and of the parallel impedance "Z".

Operations of the photodetecting circuit according to the preferred invention, as illustrated in FIG. 1, will now be described with reference to the waveforms shown in FIG. 2.

First, the light emitting diode LED flickers a rectangular pulse, as illustrated in FIG. 2k, representing reversed conditions of the clock pulse in synchronism with the clock pulse shown in FIG. 2h. Under these circumstances, the light receiving element PTR simultaneously receives not only the light coming from the light emitting diode LED but also the peripheral interfering light as illustrated in FIG. 2j, and then, the intensity of the received light for the light receiving element PTR is calculated by summing the intensity of the peripheral interfering light, as illustrated in FIG. 2i with the intensity of the light come from the light emitting element.

Under the above-described conditions the switching element "S" is closed when the light emitting diode LED is not energized. In the operational amplifier 3, the resistor R1 and the second negative feedback circuit 4 constitute a parallel negative feedback loop. Consequently, the voltage appearing at the output Vout is expressed as follows:

$$V_{OUT} = \frac{R1 \times R2}{R1 + R2} \times I3 + V \quad (1)$$

It should be noted that the resistance value of the resistor R1 is considerably higher than that of the resistor R2, for instance, $10^4$ times higher than the resistance value of the resistor R2, and the resistor R2 is, for instance, about 10 ohms. As a result, the output voltage Vout of the operational amplifier 3 is substantially equal to the reference voltage V, so that an adverse influence by the current I3 due to the peripheral interfering light can be suppressed within a small change of the output voltage as illustrated in the waveforms f1 and f2 (see FIG. 2n). That is to say, the output voltage Vout of the operational amplifier 3 is not saturated even if the peripheral interfering light having the higher intensity is received by the light receiving element PTR.

At this time, to the output of another operational amplifier 5, a voltage equal to the above-described voltage Vout of the operational amplifier 3 is output. Accordingly, the voltage equal to the voltage Vout is also applied to one end of the resistor R2 connected to the operational amplifier 5. Since, on the other hand, the other end of this resistor R2, one end of the resistor R1, one end of the operational amplifier 3 and the collector of the light receiving transistor PTR are connected to each other, the identical potential appears at this junction. Then, since the other end of the resistor R1 is connected to the output Vout of the operational amplifier 3, the potential differences between the resistors R1 and R2 are equal to each other. It is understood that in view of the so-termed "virtual ground characteristic of an operational amplifier", the voltages of the inverting input terminal (−) and the non-inverting input terminal (+) of the operational amplifier 3, are equal to the voltage of the reference voltage circuit V. As a consequence, the first and second feedback currents I1 and I2 flowing through the resistors R1 and R2 are expressed by the following equations:

$$I1 = \frac{V_{OUT} - V}{R1} \quad (2)$$

$$I2 = \frac{V_{OUT} - V}{R2} \quad (3)$$

Then, a ratio of the first feedback current I1 to the second feedback current I2 is calculated as follows.

$$\frac{I1}{I2} = \frac{\frac{V_{OUT} - V}{R1}}{\frac{V_{OUT} - V}{R2}} = \frac{R2}{R1} \quad (4)$$

As a result, it is understood that the ratio of the first feedback current to the second feedback current is equal to current inversely proportional to the respective resistance values of R1 and R2. Then, as previously described, since the resistance value of the resistor R1 is higher than that of the resistor R2 by $10^4$, the first feedback current I1 is considerably lower than the second feedback current I2. Moreover, since the photocurrent I3 flowing through the light receiving element PTR is equal to the current obtained by summing the first and second feedback currents, and the first feedback current I1 is much smaller than the second feedback current I2, the photocurrent I3 flowing through the light receiving element PTR is essentially equal to the second feedback current supplied from the second feedback current, as illustrated in FIG. 2m.

When the light emitting diode LED is energized, the switching element "S" is opened, and then, the voltage which has obtained just before the lightening of the light emitting diode LED, is held at the non-inverting input (+) of the operational amplifier 5. As a result, the output voltage of the operational amplifier 5 also keeps the voltage which has been obtained just before the lightening of the light emitting diode LED, and thus, the second feedback current I2 can hold the current which has been acquired just before the lightening of the light emitting diode LED. The photocurrent I3 flowing through the light receiving element PTR caused by the lightening of the light emitting diode LED, increases by ΔI3, as illustrated in FIG. 2m. This increased current ΔI3 is accordingly supplied by the increased current ΔI1 of the first feedback current I1 as illustrated in FIG. 2m, because the second feedback current I2 is held. In other words, the increased current component ΔI3 of the photocurrent I3 is very close to the varied component ΔI1 of the first feedback current I1, so that the varied component of the output voltage Vout is similarly very close to the voltage variation ΔVout as illustrated in FIG. 2n. At this time, the voltage variation ΔVout of the output voltage of the operational amplifier 3 is equal to a product obtained by the resistor R1 and the varied component ΔI1 of the first feedback current I1. It should be noted that the voltage of the variation of the output voltage Vout becomes greatly large, i.e., the voltage variation ΔVout, with respect to a small increased value ΔI1 of the photocurrent because the resistance of the resistor R1 is selected to be considerably large, as compared with the resistor R2. Consequently, the varied component ΔVout of the output voltage Vout of the operational amplifier 3 is correctly output with a value proportional to the illumination intensity of the light emitting diode LED, as illustrated in FIG. 2k.

In the previous preferred embodiment, the light emission by the light emitting diode was performed in synchronism with the sample-and-hold operations. It may be, however, possible that in accordance with the response speeds of the light receiving element and the light emitting element, the lightening operation is shifted from the sampling-and-hold operation.

The photodetecting circuit according to the invention has the following features. That is to say, when the light emitting element is energized, the second negative feedback circuit 4 cancels the components of the peripheral interfering light based upon the current value of the peripheral light which has obtained just before the light emitting element is turned off. Also, a constant value is negative-fed back by means of the first negative feedback circuit R1 and the photocurrent caused by the light emitting current is converted into the corresponding voltage signal by a predetermined current-to-voltage converting coefficient. As a result, under the condition that the light receiving element simultaneously receives not only the optical signal from the light emitting element but also the peripheral intensity than that of the optical signal, the light receiving current of the photodetecting circuit is not saturated at all, with the result that the optical signal come from the light emitting element can be detected in a stable condition, and moreover, the erroneous detection of the optical signal by the light receiving element can be prevented.

What is claimed is:

1. A photoconducting circuit comprising:
   a light emitting element driven by a first synchronizing on/off input signal having a predetermined period;
   a light receiving element correspondingly arranged for detecting light emitted by said light emitting element and for outputting a current signal varied in response to an amount of said light received from said light emitting element;
   a current-to-voltage converting circuit for converting said current signal from said light receiving element into a corresponding voltage output signal;
   a first negative feedback circuit for negative-feeding, at a specified first constant, said voltage output signal of said current-to-voltage converting circuit back to an input circuit of said current-to-voltage converting circuit;
   a sample-and-hold circuit for detecting and holding said voltage output signal of said current-to-voltage converting circuit, said sample-and-hold circuit being driven by a second synchronizing on/off input signal which is the complement of said first synchronizing on/off input signal;

a second negative feedback circuit for negative-feeding an output signal from said sample-and-hold circuit back to said input circuit at a second constant which is greater than said first constant of said first negative feedback circuit.

2. A photoconducting circuit as claimed in claim 1, wherein said light emitting element is a light emitting diode.

3. A photoconducting circuit as claimed in claim 1, wherein said light receiving element is a phototransistor.

4. A photoconducting circuit as claimed in claim 1, wherein said current-to-voltage converting circuit is constructed by a first operational amplifier, and said first feedback circuit is arranged by a first resistor connected to the first operational amplifier so as to feed an output signal of said first operational amplifier back to an input terminal thereof.

5. A photoconducting circuit as claimed in claim 1, wherein said sample-and-hold circuit is arranged by a second comparator, a switching element, and a capacitor.

6. A photoconducting circuit as claimed in claim 1, wherein said second feedback circuit is constructed by at least a second operational amplifier and a second resistor.

7. A photoconducting circuit as claimed in claim 1, wherein said first feedback circuit is connected parallel to said second feedback circuit.

8. A photoconducting circuit as claimed in claim 7 wherein said second operational amplifier has an output terminal and an input terminal directly connected to said output terminal, thereby functioning as a buffer amplifier.

* * * * *